United States Patent
Forster et al.

(10) Patent No.: US 7,052,672 B2
(45) Date of Patent: May 30, 2006

(54) STABILIZED RADIOPHARMACEUTICAL COMPOSITIONS

(75) Inventors: Alan Michael Forster, Amersham (GB); David Edwards, Amersham (GB); Ole Kristian Hjelstuen, Kjeller (NO)

(73) Assignee: GE Healthcare Limited, Buckinghamshire (GB)

( * ) Notice: Subject to any disclaimer, the term of this patent is extended or adjusted under 35 U.S.C. 154(b) by 277 days.

(21) Appl. No.: 10/465,974

(22) PCT Filed: Apr. 11, 2001

(86) PCT No.: PCT/GB01/01624

§ 371 (c)(1),
(2), (4) Date: Jun. 26, 2003

(87) PCT Pub. No.: WO02/053192

PCT Pub. Date: Jul. 11, 2002

(65) Prior Publication Data

US 2004/0057899 A1    Mar. 25, 2004

(30) Foreign Application Priority Data

Dec. 28, 2000   (GB) ................................ 0031592

(51) Int. Cl.
*A61K 51/00*    (2006.01)
*A61M 36/14*    (2006.01)

(52) U.S. Cl. ...................... 424/1.65; 424/1.11; 424/9.1

(58) Field of Classification Search ............... 424/1.11, 424/1.65, 1.37, 9.1, 9.3, 9.4, 9.5, 9.6, 9.7, 424/9.8; 206/223, 569, 570
See application file for complete search history.

(56) References Cited

U.S. PATENT DOCUMENTS

| | | | |
|---|---|---|---|
| 3,939,258 A | 2/1976 | Niemann | 424/1 |
| 4,233,284 A | 11/1980 | Fawzi | 424/1 |
| 4,364,920 A | 12/1982 | Winchell | 424/1 |
| 4,451,451 A | 5/1984 | Rimmer | 424/1.1 |
| 4,781,912 A | 11/1988 | Zanelli et al. | 424/1.1 |
| 5,093,105 A | 3/1992 | Flanagan et al. | 424/1.1 |
| 5,227,152 A | 7/1993 | Flanagan et al. | 424/1.1 |
| 5,420,321 A | 5/1995 | Edwards | 556/112 |

FOREIGN PATENT DOCUMENTS

EP    0508724 B1    8/1996

OTHER PUBLICATIONS

Hensel, et.al. (J Pharm Sci 1995; 84(1): 115-118).

*Primary Examiner*—Dameron L. Jones
(74) *Attorney, Agent, or Firm*—Li Cai

(57) ABSTRACT

The present invention relates to stabilized $^{99m}$Tc radiopharmaceutical compositions, which include both a radioprotectant and one or more antimicrobial preservative(s), and hence have an extended lifetime of use. The radioprotectant is ascorbic acid, para-aminobenzoic acid, gentisic acid or a salt thereof with a biocompatible cation, and the antimicrobial preservative is one or more compound from the paraben series of preservatives. The invention is particularly useful for cationic, lipophilic $^{99m}$Tc heart imaging agents such as Myoview™.

17 Claims, 4 Drawing Sheets

STABILIZED RADIOPHARMACEUTICAL COMPOSITIONS

This application is a filing under 35 U.S.C. § 371 of PCT/GB01/01624 filed Apr. 11,2001 which claims priority to Great Britain Application 0031592.9 filed Dec. 28, 2000, the entire disclosure of which is hereby incorporated by reference.

FIELD OF THE INVENTION

The present invention relates to stabilised $^{99m}$Tc radiopharmaceutical compositions, which include both a radioprotectant and one or more antimicrobial preservative(s), and hence have an extended lifetime of use.

BACKGROUND TO THE INVENTION

Diagnostic imaging radiopharmaceuticals based on the radioisotope technetium-99m ($^{99m}$Tc) are known for a variety of clinical diagnoses, including functional studies (eg. renal), and perfusion (especially heart and brain). The radioisotope $^{99m}$Tc has a half-life of 6 hours, hence such $^{99m}$Tc radiopharmaceuticals are usually prepared from so-called "kits".

These kits for the preparation of $^{99m}$Tc radiopharmaceuticals permit the user to maintain stocks of non-radioactive kits, which are designed to be reconstituted with $^{99m}$Tc-pertechnetate (TcO$_4$) from a supply of $^{99m}$Tc. A sterile solution of $^{99m}$Tc-pertechnetate in isotonic saline is obtained by elution of a technetium generator with sterile saline as is known in the art.

Kits for the preparation of $^{99m}$Tc radiopharmaceuticals typically contain:

(i) a ligand which forms a metal complex with $^{99m}$Tc,
(ii) a biocompatible reducing agent capable of reducing pertechnetate, ie. Tc(VII) to the lower oxidation state of the desired $^{99m}$Tc metal complex product.

The biocompatible reducing agent for the $^{99m}$Tc pertechnetate is typically stannous ion, ie. Sn(II). The kit may contain additional excipients, such as weak chelating agents (such as gluconate, glucoheptonate, tartrate or EDTA), stabilisers, pH-adjusting agents, buffers, solubilisers or bulking agents (such as mannitol, inositol or sodium chloride), to facilitate handling and lyophilisation of the kit components. To facilitate storage and distribution, the non-radioactive kits are usually supplied freeze-dried in a sterile vial with closure. The lyophilised formulation also permits facile reconstitution by the end users with sterile pertechnetate in saline, to give the desired sterile, injectable $^{99m}$Tc radiopharmaceutical for human use. The shelf life of the non-radioactive technetium kit may be several months.

Radiopharmaceutical compositions may suffer from radiolysis, particularly of the solvent (typically water), with consequent generation of highly reactive free radicals, which may degrade one or more components of the composition. It is known to employ radioprotectants or free radical scavengers to help suppress such degradation. Typically, free radical scavengers are taken from known classes of antioxidant compounds. Ascorbic acid and ascorbates are disclosed to function as stabilisers for stannous-containing non-radioactive kits for the preparation of $^{99m}$Tc radiopharmaceuticals in U.S. Pat. No. 4,364,920, and have subsequently been widely used in $^{99m}$Tc radiopharmaceutical preparations. Gentisic acid stabilisers for $^{99m}$Tc radiopharmaceuticals are disclosed in U.S. Pat. No. 4,233,284. Para-aminobenzoic acid (PABA) and related stabilisers for $^{99m}$Tc radiopharmaceutical preparations are disclosed in U.S. Pat. No. 4,451,451.

U.S. Pat. No. 3,939,258 (1976) teaches that the antimicrobial preservatives methylparaben and propylparaben can be added to radiopharmaceutical preparations containing the radioisotope $^{113}$In. The preparations do not contain a radioprotectant.

The commercial non-radioactive kit CHOLETEC™ for the preparation of a $^{99m}$Tc radiopharmaceutical, contains mebrofenin (4.5 mg), methylparaben (4.5 mg), propylparaben (0.5 mg) and stannous fluoride (0.73 mg) in the formulation. The kit formulation does not contain a radioprotectant. The pack leaflet also includes the statement that "If sodium pertechnetate Tc-99m injection must be diluted for use with Choletec, only Sodium Chloride Injection USP without preservatives should be used." Mebrofenin is a complexing agent for $^{99m}$Tc, which is a substituted iminodiacetic acid (IDA).

The parabens are a known series of antimicrobial preservatives:

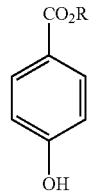

R=Me Methylparaben
Et Ethylparaben
n-Pr Propylparaben
n-Bu Butylparaben

U.S. Pat. No. 5,093,105 relates to the use of benzalkonium chloride or benzethonium chloride as radiopharmaceutical antimicrobial preservatives, which are claimed to be compatible with radioprotectants. Other antimicrobial preservatives are described in U.S. Pat. No. 5,093,105 as being incompatible with radioprotectants. Benzethonium chloride is, however, classed as a weak carcinogen and benzalkonium chloride is generally regarded as a toxic substance when administered orally.

Hensel et al. [*J Pharm Sci* 1995; 84(1):115–118] disclose that the degradation of paraben preservatives in the presence of macromolecules such as polysaccharides, and specifically via transesterification with alcohols, was a known problem. They reported that transesterification of parabens also occurs in the presence of polyols, such as xylitol, glycerol and sorbitol, but did not observe transesterification with aldoses such as ribose or xylose.

Certain radiopharmaceutical agents are particularly useful to be available in an acute situation, eg. an intensive care or emergency room (ER) setting. There is a need for some patient diagnoses to be made at any time of day or night, with ready availability of the radiopharmaceutical for the diagnostic scan, at times when conventional supply of radiopharmaceutical from a radiopharmacy may simply not be an option. For such purposes in particular, there is therefore a need for radiopharmaceuticals which can be prepared by a skilled radiopharmacist, but have a post-reconstitution shelf life of more than 12 hours, eg. up to 36 hours.

THE PRESENT INVENTION

The present invention provides an improved $^{99m}$Tc radiopharmaceutical composition, which has a post-reconstitution shelf-life of at least 24 hours. Preferred $^{99m}$Tc radiopharmaceuticals are those which have particular benefit in the acute situation, which include heart, brain, lung and thrombus imaging agents.

Solving the problem of extended post-reconstitution availability of a $^{99m}$TC radiopharmaceutical agent means that, at reconstitution, the initial level of radioactivity of $^{99m}$Tc must be high. That is because the 6 hour half-life of $^{99m}$Tc means that half the radioactivity which will be used to provide the diagnostic image is lost to radioactive decay every 6 hours, and hence only $1/16$ of the original radioactivity will remain by 24 hours. Such high levels of radioactivity for extended periods pose significant potential radiolysis problems for the $^{99m}$Tc radiopharmaceutical composition. The present invention therefore includes a radioprotectant in the composition.

The usable period post-reconstitution for injectable radiopharmaceuticals is further constrained by the potential for micro-organism growth in parenteral solutions. In order to reduce the risk of infection from multi-use solutions for human injection which are stored for extended periods (eg. longer than 12 hours), then the preparation must be stored at all times post-reconstitution either in a frozen state, or at a temperature of 2–8° C. Alternatively, a bactericide (ie. a microbiological eliminator), or a bacteriostatic agent (ie. a microbiological growth inhibitor) should be present to suppress the growth of microorganisms. Prolonged storage of the radiopharmaceutical preparation either frozen or at a guaranteed temperature of 2–8° C. at all times during transport (eg. from a radiopharmacy to the clinician), and storage prior to use is very difficult to achieve, and therefore undesirable and inconvenient on a routine basis. Hence, the present invention includes one or more antimicrobial preservative(s) in the radiopharmaceutical composition. The stabilised compositions and kits of the present invention can be stored at ambient or room temperature, ie. without special temperature storage conditions necessary to suppress growth of micro-organisms. This is a significant advantage in terms of convenience of use.

DETAILED DESCRIPTION OF THE INVENTION

The present invention provides in a first aspect, a stabilised $^{99m}$Tc radiopharmaceutical composition which comprises:
(i) a $^{99m}$Tc metal complex;
(ii) a radioprotectant which comprises ascorbic acid, para-aminobenzoic acid or gentisic acid, or a salt thereof with a biocompatible cation;
(iii) one or more antimicrobial preservatives of formula (I):

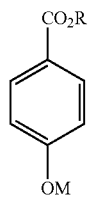

(I)

where R is $C_{1-4}$ alkyl, and M is H or a biocompatible cation.

Thus, contrary to the teaching of the prior art, it has surprisingly been found that the paraben antimicrobial preservatives of Formula (I) can be used in conjunction with radioprotectants in $^{99m}$Tc radiopharmaceutical preparations, without adverse effect on the radiochemical purity (RCP) of the $^{99m}$Tc agent (ie. significant levels of $^{99m}$Tc-based impurities), and hence the image quality.

By the term "$^{99m}$Tc metal complex" is meant a coordination complex of technetium with one or more ligands. It is strongly preferred that the $^{99m}$Tc metal complex is "resistant to transchelation", ie. does not readily undergo ligand exchange with other potentially competing ligands for the technetium coordination sites. Potentially competing ligands could be other excipients in the preparation (eg. stabilisers, radioprotectants, antimicrobial preservatives or preservatives used in non-radioactive kits). These compounds typically have oxygen or nitrogen donors which are carboxylic acids or their esters, or alcohols. Carboxylic acids and alcohols tend to form relatively weak complexes with technetium and such potentially competing ligands typically do not have the donor atoms arranged to chelate the technetium.

Suitable ligands for use in the present invention which form $^{99m}$Tc complexes resistant to transchelation include: chelating agents, where 2–6, preferably 2–4, metal donor atoms which bind to technetium are arranged such that 5- or 6-membered chelate rings result (by having a non-coordinating backbone of either carbon atoms or non-coordinating heteroatoms linking the metal donor atoms); or monodentate ligands which comprise donor atoms which bind strongly to technetium, such as isonitriles, phosphines or diazenides. Examples of donor atom types which bind well to technetium as part of chelating agents are: amines, thiols, amides, oximes and phosphines. Phosphines form such strong technetium complexes that even bidentate chelating phosphines such as Tetrofosmin (i.e. 6,9-bis(2-ethoxyethyl)-3,12-dioxa-6,9-diphosphatetradecane), form suitable $^{99m}$Tc complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as mibi (i.e. 1-isocyano-2-methoxy-2-methylpropane). Examples of suitable phosphines include Tetrofosmin, and monodentate phosphines such as tris(3-methoxypropyl)phosphine. Examples of suitable diazenides include the HYNIC series of ligands i.e. hydrazine-substituted pyridines or nicotinamides.

Examples of suitable chelating agents for technetium which form $^{99m}$Tc complexes resistant to transchelation include, but are not limited to:
(i) diaminedioximes of formula:

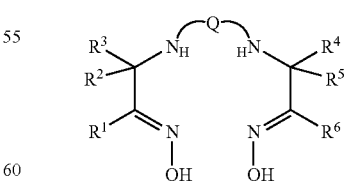

where $R^{1-R6}$ are each independently an R group;
each R is H or $C_{1-10}$ alkyl, alkylaryl alkoxyalkyl, hydroxyalkyl, fluoroalkyl or aminoalkyl,
where one or more of the R groups may optionally be conjugated to a biological targeting molecule;

and Q is a bridging group of formula —(A)$_n$—;
where n is 3, 4 or 5 and each A is independently —O—, —NR— or —CR$_2$— provided that (A)$_n$ contains a maximum of one A group which is —O— or —NR—.

Preferred diaminedioximes have R$^1$ to R$^6$=C$_{1-3}$ alkyl, alkylaryl alkoxyalkyl, hydroxyalkyl, fluoroalkyl or aminoalkyl, where one or more of the R groups may optionally be conjugated to a biological targeting molecule. Most preferred diaminedioximes have R$^1$ to R$^6$=CH$_3$ where one or more of the R groups may optionally be conjugated to a biological targeting molecule and:

Q=—(CH$_2$)$_3$— ie. propyleneamine oxime or PnAO;
Q=—(CH$_2$)$_4$— ie. butyleneamine oxime or BnAO;
Q=—(CH$_2$)$_5$ ie. pentyleneamine oxime or PentAO;
Q=—N(CH$_2$)$_2$NR(CH$_2$)$_2$N—;
or R$^1$=R$^3$, R$^5$ and R$^6$=CH$_3$, and R$^2$, R$^4$=H and Q=—CH$_2$C(CH$_3$)$_2$CH$_2$— ie. hexamethylpropyleneamine oxime or HMPAO;

(ii) N3S ligands having a thioltriamide donor set such as MAG3 and related ligands; or having a diamidepyridinethiol donor set such as Pica;

(iii) N2S2 ligands having a diaminedithiol donor set such as BAT or ECD (i.e. ethylcysteinate dimer), or an amideaminedithiol donor set such as MAMA;

(iv) N4 ligands which ore open chain or macrocyclic ligands having a tetramine, amidetriamine or diamidediamine donor set, such as cyclam, monoxocyclam or dioxocyclam.

(v) N2O2 ligands having a diaminediphenol donor set.

Preferred ligands of the present invention are phosphines, isonitriles and diaminedioximes, with Tetrofosmin and mibi (i.e. 2-methoxy-isobutylnitrile or 1-isocyano-2-methoxy-2-methylpropane) being especially preferred, and Tetrofosmin being most especially preferred. Tetrofosmin and mibi form cationic, lipophilic $^{99m}$Tc complexes which are suitable for heart imaging, and are used in the commercial products Myoview™ and Cardiolite™ respectively. By the term "cationic, lipophilic $^{99m}$Tc complex" is meant a technetium-99m co-ordination complex in which the technetium is positively charged, and the technetium complex has an octanol/water partition coefficient of greater than 0.5.

The $^{99m}$Tc ligands of the present invention may optionally be conjugated to biological targeting molecules to target the $^{99m}$Tc radiopharmaceutical to sites of interest within the mammalian body, such as particular organs, receptors or disease sites. Suitable such biological targeting molecules include: 1–100 mer peptides or peptide analogues which may be linear or cyclic, especially 3–20 mer peptides; monoclonal antibodies or fragments thereof; or enzyme substrates or inhibitors, synthetic receptor-binding compounds, oligonucleotides, or oligo-DNA or oligo-RNA fragments.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the $^{99m}$Tc radiopharmaceutical composition post-reconstitution, ie. in the radioactive diagnostic product itself. The antimicrobial preservative may, however, also optionally be used to inhibit the growth of potentially harmful micro-organisms in one or more components of non-radioactive kits of the present invention prior to reconstitution.

The paraben antimicrobial preservatives of Formula (I) of the present invention have optimal activity at a range of pH of 4–8, and are hence suitable for a wide range of $^{99m}$Tc radiopharmaceutical preparations. Parabens are effective in low concentrations against fungi (yeasts and moulds) and bacteria. They have more a static than lethal (ie. bactericidal) effect on micro-organisms. The antimicrobial preservative activity of the parabens increases as the length of alkyl chain increases. Parabens also have the advantage that, unlike the bacteriostats benzyl alcohol and chlorobutanol, they are involatile and are hence amenable to inclusion in freeze-dried formulations. Parabens are also already approved by the Regulatory Authorities for injectable radiopharmaceutical preparations. Saline solutions for human injection containing an antimicrobial preservative are commonly abbreviated as 'BSI' (bacteriostatic saline for injection). A BSI USP that contains both methyl and propyl parabens as antimicrobial preservative is commercially available from American Pharmaceutical Partners (APP). One cm$^3$ of the solution contains:

| Methylparaben | 1.2 mg, |
|---|---|
| Propylparaben | 0.12 mg, |
| Sodium chloride | 9 mg, |
| at a pH of 4.5–7.0. | |

The paraben antimicrobial preservatives of Formula (I) of the present invention may be used in either the phenol (ie. M=H), or salt form (where M=a biocompatible cation). By the term "biocompatible cation" is meant a positively charged counterion which forms a salt with an ionised, negatively charged group (here a phenolate group, ie. phenyl-O), where said positively charged counterion is also non-toxic and hence suitable for administration to the mammalian body, especially the human body. Examples of suitable biocompatible cations include: the alkali metals (eg. sodium or potassium); the alkaline earth metals (eg. calcium, magnesium and barium); and the ammonium ion. A preferred biocompatible cation is sodium. When M of Formula (I) is a biocompatible cation, the paraben antimicrobial preservative is more soluble in water. Thus, eg. the sodium salt of methylparaben is soluble 1 part in 2 parts of water, and the sodium salt of propylparaben is soluble 1 part in 1 part of water.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (ie. 2,5-dihydroxybenzoic acid) and salts thereof with a biocompatible cation as described above. Preferred radioprotectants are ascorbic acid, and sodium ascorbate. The radioprotectants of the present invention are commercially available, eg. Ascorbic Acid Injection USP is commercially available from a number of suppliers, including Abbott Laboratories.

The concentration of the paraben antimicrobial preservative of Formula (I) in the $^{99m}$Tc radiopharmaceutical solution should be sufficient to function effectively as an antimicrobial preservative, and is preferably at least 0.3 mg/cm$^3$, up to the limit of solubility of the paraben(s) in the medium. The effectiveness of a given concentration can readily be assessed using proscribed test methods, such as the USP Chapter 51 antimicrobial effectiveness testing. The solubility of certain specific parabens (with M=H) in water is:

| | |
|---|---|
| methylparaben | 2.5 mg/cm$^3$, |
| ethylparaben | 0.070% w/w at 25° C., |
| propylparaben | 1 part in 2000 parts water, |
| butylparaben | 1 part in 5000 parts water. |

Suitable paraben compositions which remain in solution in the preparation at a concentration to function effectively as antimicrobial preservatives can readily be determined based on the above aqueous solubility, the pH of the medium, the relative hydrophilic/lipophilic composition of the solution, and the desired final concentration. The pH of the medium is important since all antimicrobial preservatives have an optimal pH range. For formulations which are predominantly aqueous, methylparaben is the most suitable paraben of the M=H phenol class, since it has the highest solubility in water. The antimicrobial preservative of the present invention may suitably comprise two or more different parabens, since combinations of individual esters are known to be additive in effect. The aqueous solubility of the paraben decreases as the length of the alkyl chain increases, but the antimicrobial activity increases with the length of alkyl chain. Hence, it is preferred to use a combination of both a short and long chain paraben as the antimicrobial preservative. Such a combination provides an additive antimicrobial preservative effect and, although the longer chain paraben has more limited aqueous solubility, less is needed because it is more potent. A preferred mixture of two parabens is the combination of R=methyl and R=propyl. This combination is believed to confer both good antifungal and good antibacterial properties. The combination of methylparaben (R=methyl, and M=H) and propylparaben (R=propyl, and M=H), is especially preferred.

The concentration of radioprotectant for use in the present invention is suitably 0.0003 to 0.7 molar, preferably 0.001 to 0.07 molar, most preferably 0.002 to 0.02 molar. For ascorbic acid, this corresponds to a suitable concentration of 0.05 to 100 mg/cm$^3$, preferably 0.2 to 10 mg/cm$^3$, most preferably 0.3 to 3.0 mg/cm$^3$. For the $^{99m}$Tc radiopharmaceutical Myoview™, the preferred concentration of an ascorbic acid or ascorbate radioprotectant is in the range 0.0025 to 0.01 molar, which corresponds to 0.4 to 1.5 mg/cm$^3$ when the radioprotectant is ascorbic acid.

A $^{99m}$Tc radioactivity content suitable for diagnostic imaging is in the range 180 to 1500 MBq, depending on the site to be imaged in vivo, the uptake and the target to background ratio. For heart imaging with a $^{99m}$Tc radiopharmaceutical, ca. 1110 MBq (30 mCi) may be used for a stress study, and ca. 350 MBq (10 mCi) for a rest study. Hence, the initial $^{99m}$Tc activity in the stabilised $^{99m}$Tc radiopharmaceutical compositions of the present invention is in the range 0.2 to 100 GBq, which permits multiple dosing from the same preparation even after the radioactive decay of several half-lives of $^{99m}$Tc.

In a second aspect, the present invention provides the stabilised $^{99m}$Tc radiopharmaceutical compositions in a sterile form suitable for human administration in either a container or a pre-filled syringe. Such pre-filled syringes contain a single human dose, and are preferably a disposable or other syringe suitable for clinical use. The pre-filled syringe may optionally be provided with a syringe shield to protect the operator from radioactive dose. Suitable such radiopharmaceutical syringe shields are known in the art and preferably comprise either lead or tungsten.

The stabilised $^{99m}$Tc radiopharmaceutical composition in a sterile form suitable for human administration may alternatively be provided in a container which has a seal which is suitable for multiple puncturing with a hypodermic needle (e.g. a crimped-on septum seal closure). Such containers may contain single or multiple patient doses. Preferred such containers comprise a single bulk vial (e.g. of 10 to 30 cm$^3$ volume) which contains multiple patient doses, whereby single patient doses can thus be withdrawn into clinical grade syringes at various time intervals during the viable lifetime of the stabilised preparation to suit the clinical situation.

In a third aspect, the present invention provides non-radioactive kits for the preparation of the stabilised $^{99m}$Tc radiopharmaceutical composition. Such kits suitably comprise conventional freeze-dried vials for the preparation of $^{99m}$Tc radiopharmaceuticals, together with one or more additional containers comprising the radioprotectant and paraben antimicrobial preservative, together with preparation instructions. The kit may optionally be reconstituted first with either $^{99m}$Tc-pertechnetate in saline, or BSI (i.e. bacteriostatic 0.9% saline for injection). For Myoview™, both options were found to be viable, but it was preferable to form the $^{99m}$Tc-tetrofosmin complex first, and then add the BSI, since this resulted in a slightly higher radiochemical purity (RCP) than the reverse order of addition.

The radioprotectant may alternatively be added to the radiopharmaceutical kit preparation at any convenient stage. The radioprotectant is suitably either incorporated from the outset in the kit formulation, or added after formation of the $^{99m}$Tc-radiopharmaceutical. As with the paraben antimicrobial preservative, however, it is preferred to add the radioprotectant to the radiopharmaceutical preparation as soon as conveniently possible post-reconstitution, since delay in adding the radioprotectant increases the risk of degradation. For Myoview™, the radioprotectant is preferably added within 15 minutes of radioactive reconstitution.

Alternatively, one or both of the radioprotectant and antimicrobial preservative may optionally be included in the lyophilised formulation of the non-radioactive kit.

In a further aspect the present invention provides the use of a composition which comprises a combination of:
(i) a radioprotectant which comprises ascorbic acid, para-aminobenzoic acid or gentisic acid, or a salt thereof with a biocompatible cation;
(ii) one or more antimicrobial preservatives of formula (I)

(I)

where R is C$_{1-4}$ alkyl,
and M is H or a biocompatible cation;
to both stabilise and inhibit the growth of micro-organisms in $^{99m}$Tc radiopharmaceutical preparations.

The invention is illustrated by the non-limiting Examples detailed below.

Example 1 shows that no evidence was found from $^{13}$C NMR studies for any significant reaction between ascorbic acid and methylparaben, or any significant hydrolysis in more concentrated solution, even at a pH of approximately 9.6 after 7 days. Hensel et al. [*J. Pharm Sci* 1995; 84(1):

115–118] have reported that the reactivity of the parabens in a transesterification reaction with polyols was higher for those paraben esters with short chain alkyl groups. This indicates that, if any reaction were to be observed with ascorbic acid, it would be expected for the methyl ester as opposed to longer alkyl chain analogues.

Example 2 shows that parabens and ascorbic acid together in the $^{99m}$Tc radiopharmaceutical Myoview™, have no significant adverse effect on the radiochemical purity (RCP) of the preparation, even at 24 hours post-reconstitution. Examples 3 and 4 show that the preparations of the present invention do indeed function as antimicrobial preservatives by suppressing bacterial growth of non-radioactive preparations to which bacteria had been deliberately added.

Example 5 shows that the reconstituted radioactive formulation of MYOVIEW24 incorporating $^{99m}$Tc shows antimicrobial effectiveness against test bacterial species, including *Escherichia coli, Pseudomonas aeruginosa, Pseudomonas stutzeri, Staphylococcus aureus* and *Micrococcus luteus*. MYOVIEW24 is a stabilised Myoview™ preparation containing ascorbic acid (AA) as radioprotectant and Bacteriostatic Sodium Chloride 0.9% as preservative. The concentration of all the bacteria in MYOVIEW24 was reduced by at least two log factors at 72 hours in both vials and syringes when compared to the control vials and syringes containing normal saline (Table 1). The yeast and mould species did not increase in population during the duration of the study (14 days). The two species tested were *Candida albicais* and *Aspergillus niger*. The proliferation of micro-organisms in a reconstituted Myoview™ preparation was thus effectively controlled.

Example 6 shows that the biodistribution of a stabilised Myoviewm preparation of the present invention is entirely equivalent to that of the unstabilised Myoview™ product.

Example 7 shows that parabens and gentisic acid together in the $^{99m}$Tc radiopharmaceutical Myoview™, have no significant adverse effect on the radiochemical purity (RCP) of the preparation, even at 24 hours post-reconstitution. The RCP is above 90% both at 15 minutes and 24 hours post reconstitution.

EXAMPLE 1

Figure 1:
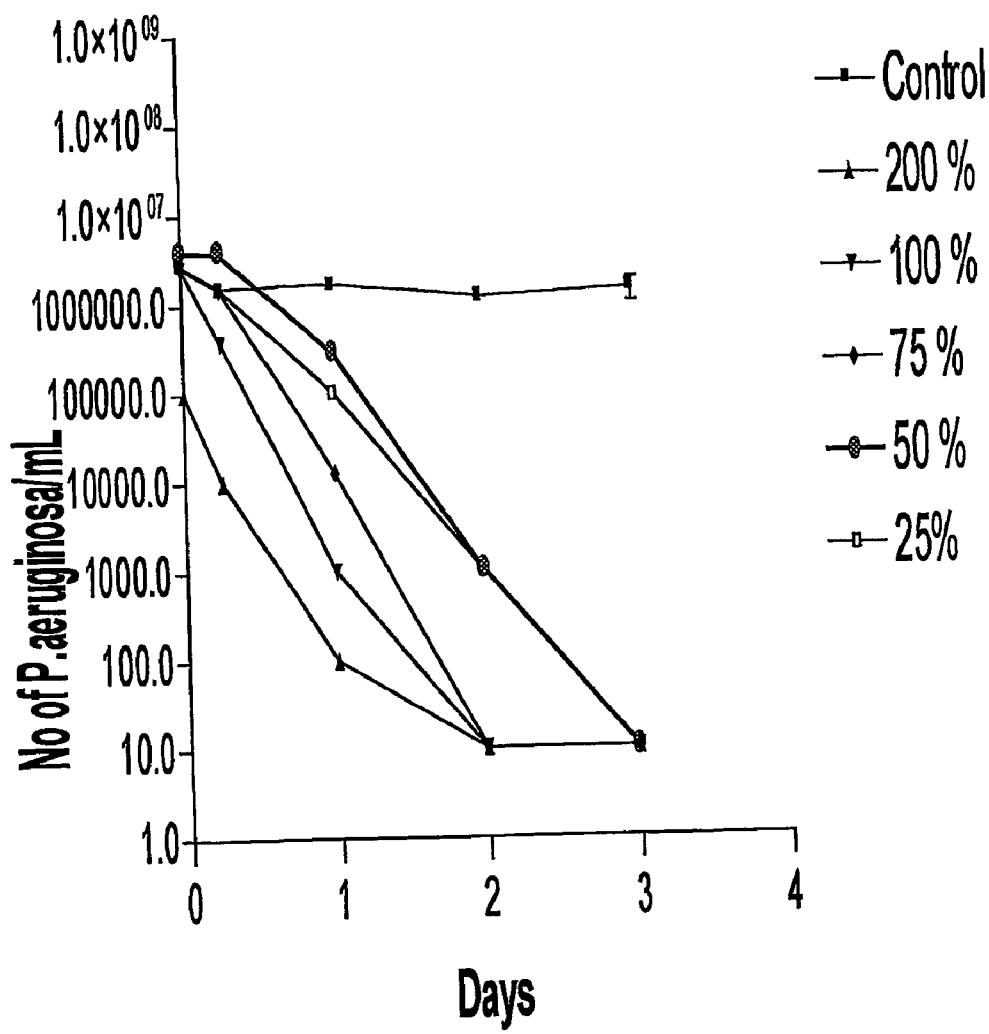
FIG. 1 shows the antimicrobial effectiveness vs *P. aeruginosa* of 25–200% BSI added to Myoview™/ascorbic acid and stored in syringes.

A $^{13}$C NMR Investigation of the Reaction Between Ascorbic Acid and Methylparaben.

Experiment A. Ascorbic acid (1.0 g) and methylparaben (48 mg) were mixed in distilled water (2.1 cm$^3$). Small portions of powdered sodium hydroxide were added with agitation to adjust the pH. At 3 defined pH's (pH 7.5, 8.8 and 9.6), a representative aliquot (0.5 cm$^3$) was transferred to an NMR tube. The 3 sampled reaction mixtures were monitored daily for one week by $^{13}$C NMR When not being monitored, the mixtures were stored at room temperature protected from light. At the end of the monitoring period a small quantity of methanol was added to the solution to confirm that, if hydrolysis had occurred, the $^{13}$C NMR signal for any methanol produced by transesterification would have been well separated from that for the initial methyl ester resonance.

At pH 7.5 the paraben had limited solubility so it was necessary to ensure efficient mixing of the components before removing the sample aliquot. The intensity of the signals for the paraben in the $^{13}$C NMR spectrum of this sample were also substantially reduced for similar reasons.

The $^{13}$C NMR spectra were obtained using a JEOL EX270 NMR spectrometer with a broad-band tuneable probe operating at a frequency of 67.94 MHz. The data for each spectrum was acquired over a period of about 30 min.

Experiment B. Powdered sodium hydroxide was added in small portions to a vigorously stirred mixture of ascorbic acid (100 mg) and methylparaben (100 mg) in water (2.0 cm$^3$) until a constant pH of 9.5 was obtained. An aliquot (0.5 cm$^3$) of the colourless solution was removed and monitored by $^{13}$C NMR spectroscopy. As part of the monitoring process the sample was placed in a Bruker AM250 NMR spectrometer after 29 hours and its $^{13}$C NMR spectrum accumulated over a period of 16 hours. The processed data gave a spectrum with a signal to noise ratio of 230:1. This spectrum showed that no significant quantities of any additional components had been produced from the interaction of the two components, and also that, there was no evidence for the formation of any methanol from hydrolysis of the methyl parabens. A small quantity of methanol was then added to the sample as a reference peak.

The following resonances were observed in the NMR spectra: $\delta_c$ (H$_2$O) 51.9, 62.7, 69.6, 78.4, 113.2, 115.0, 118.2, 132.1, 169.9, 171.1, 175.5, 177.4 [shifts are in ppm. relative to MeOH at 49 ppm.]. The resonances at 62.7, 69.6, 78.4, 113.2, 175.5 and 177.4 are due to ascorbate while the remaining signals are due to methylparaben.

EXAMPLE 2

Effect on the Radiochemical Purity of a Myoview™ Kit

Myoview™ is a lyophilised formulation containing:

| | |
|---|---|
| Tetrofosmin | 0.23 mg |
| Stannous chloride dihydrate | 0.03 mg |
| Disodium sulfosalicylate | 0.32 mg |
| Sodium-D-gluconate | 1.0 mg |
| Sodium hydrogen carbonate | 1.8 mg |
| pH | 8.3–9.1, | which is sealed under nitrogen gas USP/NF in a 10 ml glass vial, which upon reconstitution with Sterile Sodium ($^{99m}$Tc) Pertechnetate Injection USP/Ph.Eur., yields a solution containing the heart imaging radiopharmaceutical $^{99m}$Tc-tetrofosmin.

A Myoview™ preparation containing ascorbic acid and parabens was prepared as follows:
  (i) ascorbic acid USP solution (500 mg/cm³, 0.5 cm³) was added by syringe to a vial containing Bacteriostatic Saline for Injection USP [1.2% (w/v) methyl paraben, 0.12% (w/v) propyl paraben in 0.9% (w/v) sodium chloride solution; 10 cm³];
  (ii) a conventional Myoview™ vial was reconstituted with $^{99m}$Tc-pertechnetate in saline from a $^{99m}$Tc generator (1.5–5.0 cm, 30–400 mCi/cm³);
  (iii) within 5 minutes of the reconstitution of Step (ii), an aliquot of the solution from Step (i) (0.2 cm³) was added to the reconstituted Myoview™ vial of Step (ii);
  (iv) a further volume of BSI which is equal to the volume of eluate used in Step (ii) (1.5–5.0 cm³) was added to the solution from Step (iii) to give a MYOVIEW24 preparation.

MYOVIEW24 is a stabilised Myoview™ preparation containing ascorbic acid (AA) as radioprotectant and Bacteriostatic Sodium Chloride 0.9% (BSI) as preservative.

The radiochemical purity (RCP) was then determined by ITLC (instant thin layer chromatography), and PC (paper chromatography), as per the Myoview™ pack leaflet. The radiochemical profile of MYOVIEW24 in ITLC and PC is the same as that of regular Myoview™, with the same variation in the same minor impurities as the original product. At 30 min post-labelling, the radiochromatograms are similar, although the MYOVIEW24 preparation in this particular case gave a RCP of 94% and the normal Myoview™ labelling had an RCP of 96% for the desired $^{99m}$Tc-tetrofosmin complex. At 24 and 30 hours after labelling, the RCP of the MYOVIEW24 preparation is almost constant compared to the initial labelling—ie. still greater than 90%.

EXAMPLE 3

Figure 2:
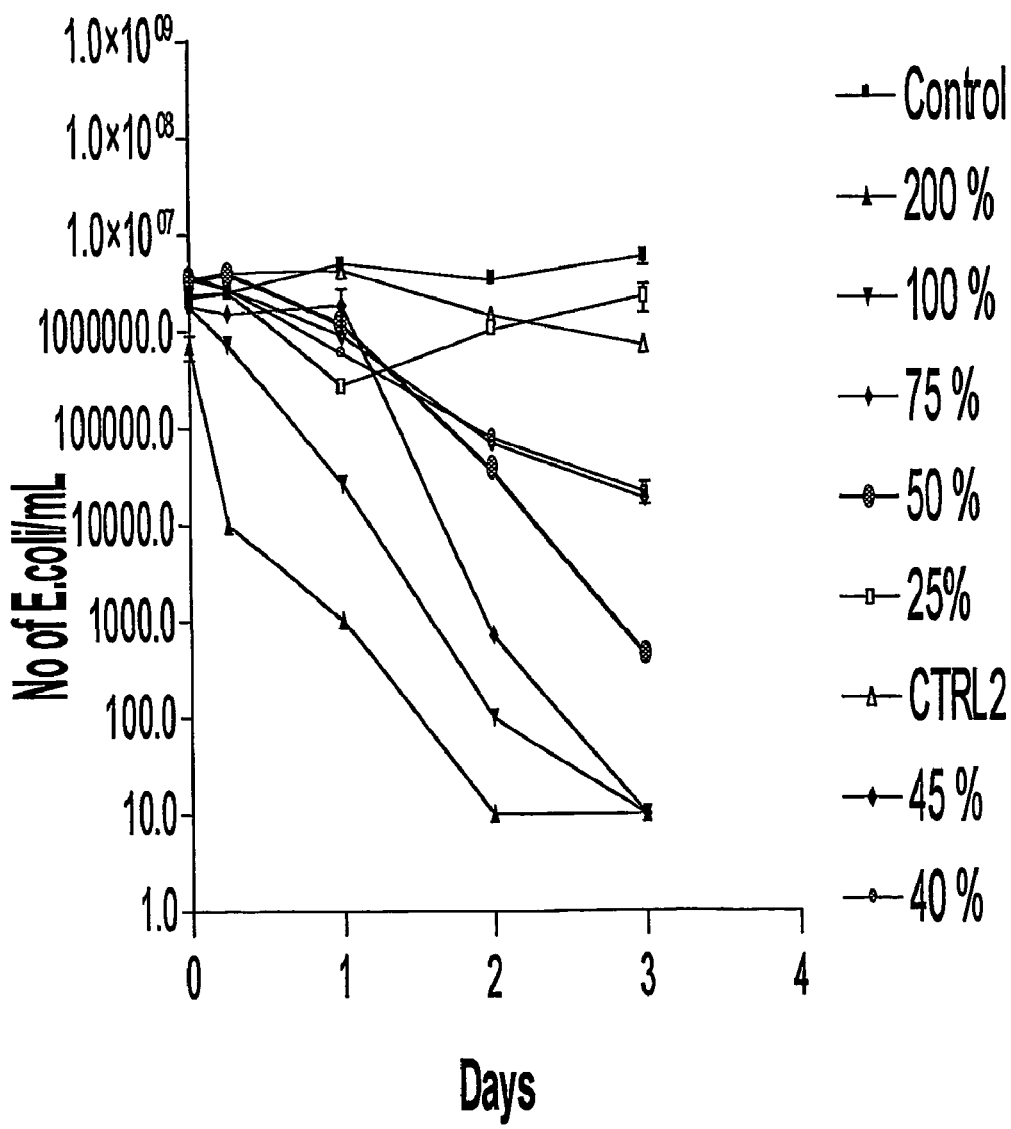
FIG. 2 shows the antimicrobial effectiveness vs *E. coli* of 25–200% BSI added to Myoview™/ascorbic acid and stored in syringes.

Antimicrobial Effectiveness: Gram-Negative Bacteria and Non-Radioactive Preparation A range of concentrations of parabens corresponding to 25–200% of the parabens concentration of BSI (1.2 mg/cm³ methylparaben and 0.12 mg/cm³ propylparaben) were added to a non-radioactive kit for the preparation of Myoview™, to which ascorbic acid (4.76 mg) had been added. Gram-negative bacteria (1×10⁶ cfu/vial; where cfu is colony forming units) were added, the product dispensed into vials and syringes, and then incubated for 72 hours at 37° C. All concentrations showed effectiveness corresponding to more than 1 log reduction in bacterial counts at 72 hours after incubation in syringes (FIG. 1) and vials for *P. aeruginosa*. For *E. coli*, all concentrations above 40% BSI showed antibacterial effectiveness corresponding to more than 1 log reduction at 72 hours after incubation in syringes (FIG. 2) and vials.

EXAMPLE 4

Antimicrobial Effectiveness: Non-Radioactive Preparation

Figure 3:
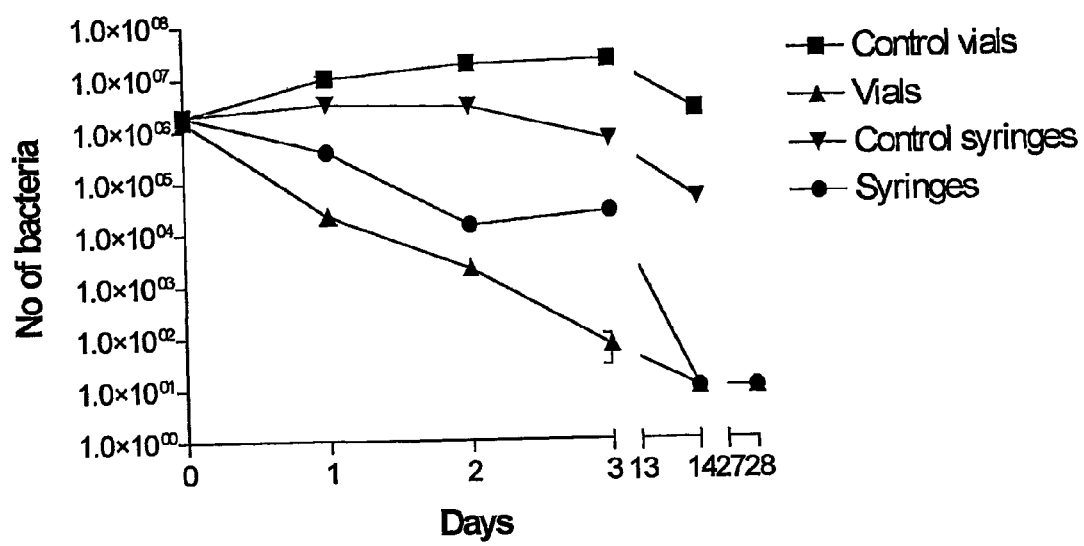
FIG. 3 shows that a non-radioactive MYOVIEW24 formulation of the present invention is effective against a microbial challenge with *E. coli*.
Figure 4:
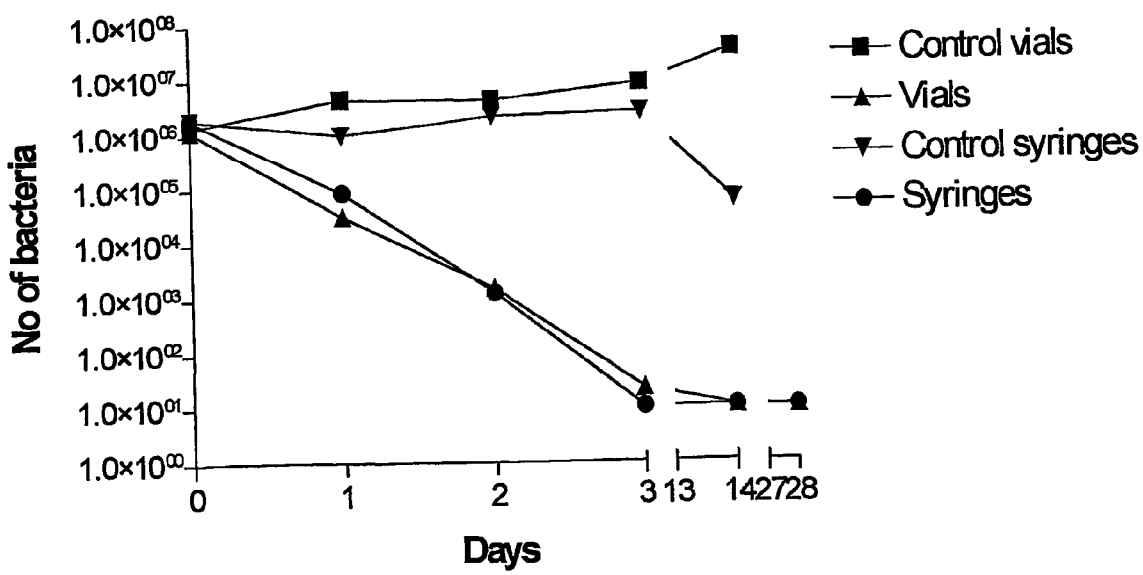
FIG. 4 shows that a non-radioactive MYOVIEW24 formulation of the present invention is effective against a microbial challenge with *P. aeruginosa*.

The MYOVIEW24 formulation of Example 2 containing 50% BSI, was challenged with six micro-organisms as specified in USP <51>, ie. *E. coli, P. aeruginosa Staph. aureus, A. niger, C. albicans* and *M. luteus*. The incubates were stored in syringes and vials. The product showed more than 1 log reduction in all bacterial counts in 72 hours and more than 2 log reduction after 14 days. FIGS. 3 and 4 show representative data for *E. coli* and *P. aeruginosa* respectively. For yeasts and moulds, there was no increase in microbial counts at any time.

EXAMPLE 5

Antimicrobial Effectiveness: Radioactive Preparation

Vials of reconstituted MYOVIEW24 prepared as per Example 2, were inoculated with 100 µL (1.0% of the total volume) of standardized inocula (six micro-organisms as specified in USP <51>, ie. *E. coli, P. aeruginosa Staph. aureus, A. niger, C. albicans* and *M. luteus*), and mixed. Three vials were prepared for each organism. The inoculum of each organism was estimated to be $1.0 \times 10^7$ to $1.0 \times 10^8$ CFU/mL, so that when the inoculum was added to the MYOVIEW24 vials, the final concentration of the test preparation was between $10^5$ and $10^6$ CFU/mL of the product per ml of the product.

An aliquot (3 ml) from each vial of inoculate was placed into a 3 ml plastic syringe, and the remaining 7 ml of inoculate was dispensed into an evacuated vial. Triplicate such syringes and vials were prepared for each organism.

Six vials of Myoview™ were inactively reconstituted with 10 ml of normal saline and Ascorbic Acid Injection USP solution (concentration 500 mg/ml AA, 9 mg/ml sodium chloride and 5 mg/ml sodium hydrosulfite at a pH of 5.5–7.0), and then were inoculated with the same inocula as above for positive controls during the test (ie. without preservative). The positive controls were not prepared with Technetium-99m. The volume was dispensed into vials and syringes as above.

Negative controls were prepared as duplicates of saline filled Myoview™ vials without inocula. The volume was dispensed into syringes and vials as above. One set of syringe/vial was incubated and plated onto TSA (Tryptone Soya Agar) as the bacteria species. One set of syringe/vial was incubated and plated onto SDA (Saboraud Dextrose Agar) TSA as the mould and yeast species.

All syringes and vials were maintained at 22.5±2.5° C. until sampled. Samples of each syringe and vial were removed according to the protocol at time 0, 6, 24 and 72 hours, plus 7 and 14 days. A 48 hour sample was removed for *C. albicans, A. niger* and *P. stutzeri*. The samples were plated with molten growth media, cooled and incubated. The number of organisms recovered was recorded. The log reduction is shown in Table 1:

TABLE 1

| Log Reduction at 72 hours and Seven days | | | | |
|---|---|---|---|---|
| | Log reduction –72 hours | | Log reduction –Seven days | |
| Test Organism | Vials | Syringes | Vials | Syringes |
| *Candida albicans* | 1.3 | 0.7 | 0.9 | 0.9 |
| *Aspergillus niger* | 2.0 | 1.7 | 2.8 | 2.8 |
| *Escherichia coli* | 5.1 | 5.2 | 5.1 | 5.2 |
| *Pseudomonas aeruginosa* | 5.0 | 5.5 | 5.0 | 5.5 |
| *Pseudomonas stutzeri* - 1 | 4.5 | 4.7 | 4.5 | 4.7 |
| *Pseudomonas stutzeri* - 2 | 6.2 | 6.0 | 6.2 | 6.0 |
| *Staphylococcus aureus* | 2.3 | 3.1 | 4.4 | 4.7 |
| *Micrococcus luteus* | 2.4 | 3.7 | 2.3 | 4.3 |
| Negative Controls | NA | NA | NA | NA | where NA = not applicable

EXAMPLE 6

Comparative Biodistribution for Myoview and Myoview24

A Myoview™ vial was reconstituted with eluate from Amertec II $^{99m}$Tc generators to give a final radioactive concentration of 5.4 mCi/cm$^3$ (0.2 GBq/cm$^3$) (normal activity) or 64.9 mCi/cm$^3$ (2.4 GBq/cm$^3$) (high activity). MYOVIEW24 was prepared as per Example 2 with eluate from $^{99m}$Tc generators to give a final radioactive concentration of 33.8 mCi/cm$^3$ (1.25 GBq/cm$^3$) (normal activity) or 64.9 mCi/cm$^3$ (2.4 GBq/cm$^3$) (high activity). The RCP of all preparations was measured within 15 to 30 minutes post-reconstitution and immediately after use at 1 hour post-reconstitution and was found in all cases to be greater than 90%. Wistar rats weighing 150–200 g were lightly anaesthetised (halothane) and injected intravenously with 0.15 cm$^3$ reconstituted Myoview™ or MYOVIEW24 via a lateral tail vein. The percentage of the injected radioactivity (expressed as % injected dose) was determined by dissection and assay for radioactivity using a twin crystal gamma counter at 2 min, 20 min, 1 hour and 7 hours after injection of normal activity preparations, or 24 hours after injection of high activity preparations. The results of the percentage of the injected radioactivity in each organ or tissue revealed that there was no significant difference in the biodistribution of $^{99m}$Tc-tetrofosmin administered as Myoview™ or MYOVIEW24 in either male or female rats. Both Myoview™ and MYOVIEW24 showed:

(i) during the first two minutes after injection the radioactivity in the blood rapidly decreased to less than 2% of the injected dose;
(ii) the amount of radioactivity in the heart is approximately 1.5% at two minutes post-injection (p.i.), reducing to about 0.8% by 7 hours p.i;
(iii) by 24 hours post injection whole body elimination is approximately 75% (60% faecal; 15% urinary). The principal site of retained radioactivity at this time is the skeletal muscle.

Figure 5:
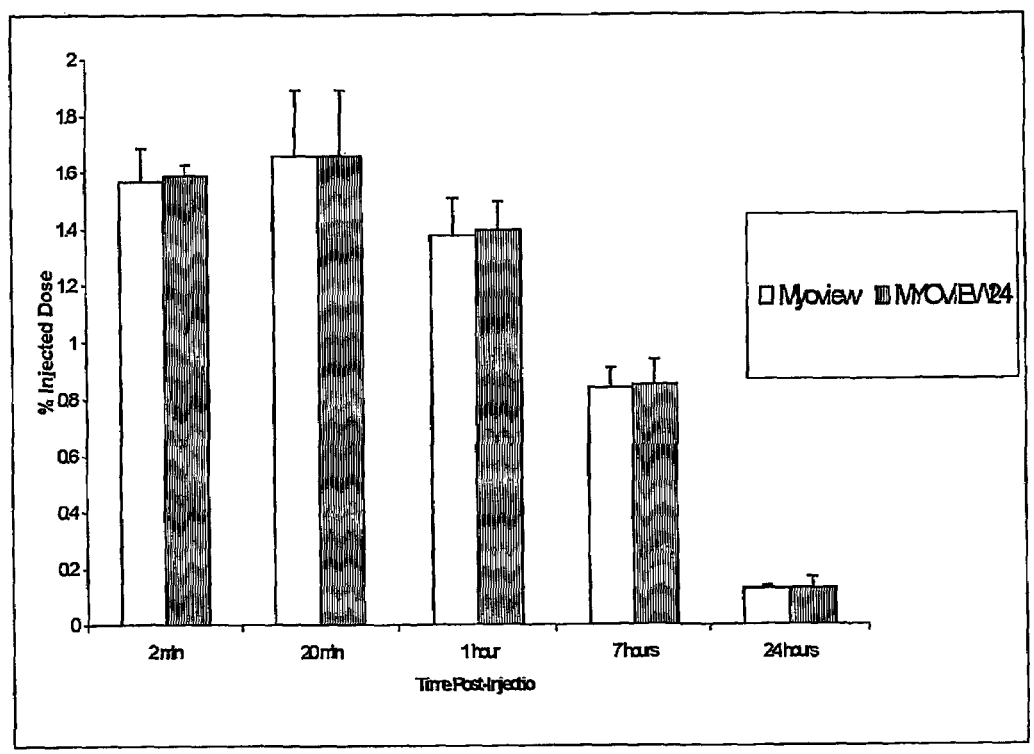
FIG. 5 shows a comparison of the percentage injected dose of $^{99m}$Tc-tetrofosmin administered as Myoview™ or MYOVIEW24 in the hearts of Wistar rats (female, mean±standard deviation, n=3), which indicate that the added antimicrobial preservative and radioprotectant have no significant effect.

FIG. 5 illustrates the equivalent biodistribution data for Myoview™ and MYOVIEW24 in the organ of interest for Myoview, ie. the heart.

EXAMPLE 7

Effect of Gentisic Acid and Parabens on the Radiochemical Purity of a Myoview™ Kit.

The effect of gentisic acid (GA) as the radioprotectant instead of ascorbic acid (AA), in combination with parabens in a stabilised Myoview™ kit was studied, in an analogous manner to Example 2. Thus, one vial of a Myoview™ kit was reconstituted with $^{99m}$Tc-eluate (1.5 ml), gentisic acid (5 mg in 0.2 ml of BSI), and BSI (1.5 ml). The RCP was analysed according to Example 2, with the preparations stored at ambient temperature between analysis. The results are as follows:

|  | Time post reconstitution | |
|---|---|---|
|  | 15 min | 24 hours |
| RCP of $^{99m}$Tc-tetrofosmin (n = 3) | 90.9% | 91.3% |

What is claimed is:

1. A stabilised radiopharmaceutical composition which comprises:
   (i) a $^{99m}$Tc metal complex;
   (ii) a radioprotectant which consists of ascorbic acid, para-aminobenzoic acid or gentisic acid, or a salt thereof with a biocompatible cation;
   (iii) one or more antimicrobial preservatives of formula (I):

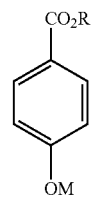

where R is $C_{1-4}$ alkyl,
   and M is H or a biocompatible cation.

2. The stabilised radiopharmaceutical composition of claim 1, where the radioprotectant is ascorbic acid or an ascorbate salt thereof with a biocompatible cation.

3. The stabilized radiopharmaceutical composition of claim 1 wherein the $^{99m}$Tc metal complex is a cationic, lipophilic $^{99m}$Tc complex.

4. The stabilised radiopharmaceutical composition of claim 1, where the $^{99m}$Tc metal complex is neutral.

5. The stabilised radiopharmaceutical composition of claim 3, where the cationic, lipophilic $^{99m}$Tc metal complex is chosen from:
   $TcO_2(tetrofosmin)_2^+$, and
   $Tc(1\text{-isocyano-2-methoxy-2-methylpropane})_6^+$.

6. The stabilised radiopharmaceutical composition of claim 1, where M is H.

7. The stabilised radiopharmaceutical composition of claim 6, where the antimicrobial preservative consists of methylparaben, ethylparaben, propylparaben, butylparaben or a combination thereof.

8. The stabilised radiopharmaceutical composition of claim 7, where the antimicrobial preservative consists of a combination of methylparaben and propylparaben.

9. A stabilised $^{99m}$Tc radiopharmaceutical composition which comprises:
   (i) $TcO_2(tetrofosmin)_2^+$,
   (ii) a radioprotectant which consists of ascorbic acid or an ascorbate salt thereof with a biocompatible cation;
   (iii) one or more antimicrobial preservatives of formula (I) of claim 1.

10. The stabilised $^{99m}$Tc radiopharmaceutical composition of claim 9, where the antimicrobial preservative consists of a combination of methylparaben and propylparaben.

11. A sterile radiopharmaceutical preparation suitable for human administration which comprises the stabilised $^{99m}$Tc composition of claim 1 in solution in a pre-filled syringe.

12. A sterile radiopharmaceutical preparation suitable for human administration, which comprises the stabilised $^{99m}$Tc composition of claim 1 in a container.

13. A non-radioactive kit for the preparation of the sterile radiopharmaceutical composition of claim 11 which comprises:
   (i) a ligand which forms the $^{99m}$Tc metal complex,
   (ii) a radioprotectant which consists of ascorbic acid, para-aminobenzoic acid or gentisic acid, or a salt thereof with a biocompatible cation,
   (iii) a antimicrobial preservative of formula (I) of claim 1; provided in sterile form in one or more containers.

14. The non-radioactive kit of claim 13, where the ligand is chosen from tetrofosmin or 1-isocyano-2-methoxy-2-methylpropane.

15. The non-radioactive kit of claim 13, where the antimicrobial preservative consists of methylparaben, ethylparaben, propylparaben or a combination thereof.

16. The radioactive kit of claim 13, where one or more of the kit components is lyophilised.

17. A method of both stabilizing and inhibiting the growth of micro-organisms in $^{99m}$Tc radiopharmaceutical preparations which comprises the addition of a combination of:

(i) a radioprotectant which consists of ascorbic acid, para-aminobenzoic acid or gentisic acid, or a salt thereof with a biocompatible cation;

(ii) one or more antimicrobial preservatives of formula (I)

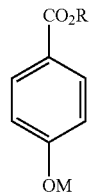

(I)

where R is $C_{1-4}$ alkyl,
and M is H or a biocompatible cation;
to said $^{99m}$Tc radiopharmaceutical preparations.

* * * * *